United States Patent [19]
Goodman et al.

[11] Patent Number: 5,322,070
[45] Date of Patent: Jun. 21, 1994

[54] BARIUM ENEMA INSUFFLATION SYSTEM

[75] Inventors: John Goodman, Huntington; Arthur Zimmet, Centerport; Matthew Froehlich, Kings Park, all of N.Y.

[73] Assignee: E-Z-EM, Inc., Westbury, N.Y.

[21] Appl. No.: 933,347

[22] Filed: Aug. 21, 1992

[51] Int. Cl.⁵ .................. A61B 10/00; A61M 13/00
[52] U.S. Cl. .................................. 128/747; 128/654; 604/26; 604/37; 604/212; 604/216; 604/246; 604/247; 604/259; 606/197
[58] Field of Search ............... 128/654, 655, 656, 747, 128/200.22; 606/197; 604/26-28, 36-37, 32-34, 45, 54, 73, 97-99, 212-213, 216, 217, 245, 246, 247, 259, 262, 275

[56] References Cited

U.S. PATENT DOCUMENTS

| | | | |
|---|---|---|---|
| 3,730,645 | 5/1973 | Mashakarn et al. | 604/26 |
| 3,769,962 | 11/1973 | McVey | 128/654 |
| 3,858,572 | 1/1975 | Binard et al. | 604/26 |
| 3,870,072 | 3/1975 | Lindemann | 604/26 |
| 3,885,590 | 5/1975 | Ford et al. | 128/654 |
| 4,048,992 | 9/1977 | Lindemann et al. | 604/26 |
| 4,090,502 | 5/1978 | Tajika | 128/654 |
| 4,258,721 | 3/1981 | Parent et al. | 128/747 |
| 4,419,099 | 12/1983 | Miller | 604/275 |
| 4,464,169 | 8/1984 | Semm | 604/26 |
| 4,676,774 | 6/1987 | Semm et al. | 604/26 |
| 5,006,109 | 4/1991 | Douglas et al. | 604/26 |
| 5,013,294 | 5/1991 | Baier | 604/26 |

FOREIGN PATENT DOCUMENTS 2733650 2/1979 Fed. Rep. of Germany ...... 128/747

Primary Examiner—Lee S. Cohen
Assistant Examiner—K. M. Pfaffle
Attorney, Agent, or Firm—McAuley Fisher Nissen Goldberg & Kiel

[57] ABSTRACT

An improved enema insufflation system includes a source of barium sulfate suspension connected, by tubing, to a multi-lumen enema tip and a source of carbon dioxide, connected to the enema tip. The carbon dioxide source contains compressed carbon dioxide. The source is connected to a carbon dioxide reservoir capable of holding a pre-determined volume of carbon dioxide at a relatively low pressure. A hand actuated insufflation bulb is connected to the carbon dioxide reservoir. The insufflation bulb can draw carbon dioxide from the reservoir for delivery, through the enema tip, to a patient. The compressed, high-pressure carbon dioxide is functionally isolated from the patient to ensure patient safety.

25 Claims, 2 Drawing Sheets

BARIUM ENEMA INSUFFLATION SYSTEM

BACKGROUND OF THE INVENTION

The present invention relates to an improved insufflation system for use in double contrast barium enema studies.

Barium enemas are used by radiologists to diagnose abnormalities of the colon. There are both single and double contrast studies. Presently the double contrast study is the more practiced form of barium enema study. In a double contrast barium enema, a barium sulfate suspension is delivered, transrectally, into the patient's colon. The suspension is delivered through the central lumen of a multi-lumen enema tip. The barium sulfate suspension is held in a plastic bag which is suspended above the patient on a pole. The barium flow is controlled with a hand activated tubing clamp located on a tube that couples the plastic bag to the enema tip.

In a double contrast study, barium sulfate suspension is delivered into the colon to coat the colon lining. The colon is a collapsible, sack-like structure. To better visualize the colon after delivery of the barium, air is delivered to the colon through a separate lumen in the enema tip. The barium coating on the walls of the colon provide radiopacity to the colon and the air serves to expand the colon. Together the barium and the air provide a clinically useful radiographic image.

As double contrast studies are presently performed, ambient air is delivered into the colon using a hand-held delivery bulb. One problem with double contrast barium enema studies is that the insufflated air distends the colon and this distention, along with gas cramps from the air, causes considerable patient discomfort which may continue for some hours after the procedure. This patient discomfort makes it more difficult to get patients to have barium enema studies when these studies are medically indicated. Since these studies are used to diagnose, among other things, colon cancer, it is imperative to get patients to have the study performed when needed.

It is known in the art that carbon dioxide can be used instead of air to perform a double contrast barium enema study. The use of carbon dioxide minimizes patient discomfort because carbon dioxide is absorbed by the body, through the colon, at a rate of about 150 times faster than air and thus both the distention and gas cramps are minimized.

Carbon dioxide, although better for patient comfort, presents certain problems. In order for carbon dioxide to be used in a radiology suite or hospital the carbon dioxide must be contained under considerable pressure. This allows a large volume of the gas to be held in a small space. The colon is a fragile structure which can be damaged if inflated to pressures in excess of 90 mmHg (less than 2 psi). If the pressurized carbon dioxide were directly coupled to a patient there would be considerable safety issues associated with possible over-insufflation of the colon and attendant damage thereto.

Accordingly it is an object of the present invention to provide a system for safely, inexpensively, and efficiently delivering carbon dioxide into a patient during a double contrast barium enema procedure.

Still another object of the present invention is to provide such a system where the high pressure carbon dioxide is functionally isolated from the patient.

A further object of this invention is to provide such a system where the system is relatively compact and portable.

BRIEF DESCRIPTION OF THE INVENTION

In one embodiment of the present invention an improved enema insufflation system is provided. The enema insufflation system is of the type which includes a source of barium sulfate suspension connected, by tubing, to a multi-lumen enema tip. The enema tip allows the delivery of either barium sulfate suspension or carbon dioxide to a patient. In the present invention compressed carbon dioxide is connected to a carbon dioxide reservoir capable of holding a pre-determined volume of carbon dioxide at a relatively low pressure. Insufflation means is connected to the carbon dioxide reservoir. The insufflation means can draw carbon dioxide from the reservoir for delivery, through the enema tip, to a patient. The compressed, high pressure, carbon dioxide is functionally isolated from the patient.

DESCRIPTION OF THE PREFERRED EMBODIMENT

Figure 1:
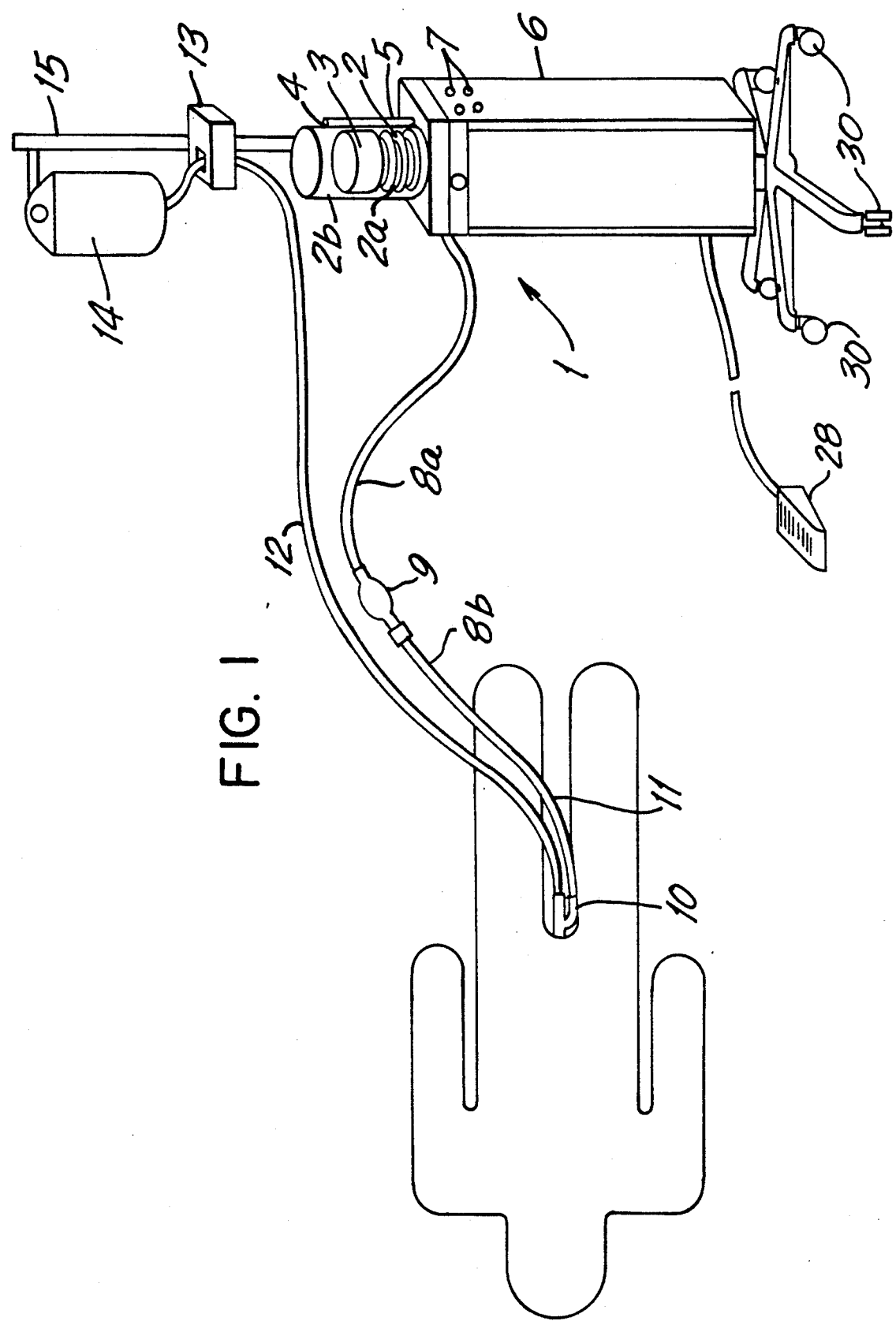
FIG. 1 is a schematic drawing showing the enema insufflation system of the present invention.

Referring now to the drawings the reference numeral 1 generally denotes the enema insufflation system of the present invention.

Compressed liquified carbon dioxide is held in a cylinder 16. In the preferred embodiment of the invention cylinder 16 is a disposable TA4 cylinder which provides adequate carbon dioxide for over 500 barium enema studies. The pressure of the carbon dioxide in cylinder 16 is about 840 psi. Cylinder 16 is small enough to be housed in a relatively small housing 6 so that system 1 can be easily moved about a radiology suite.

Figure 2:
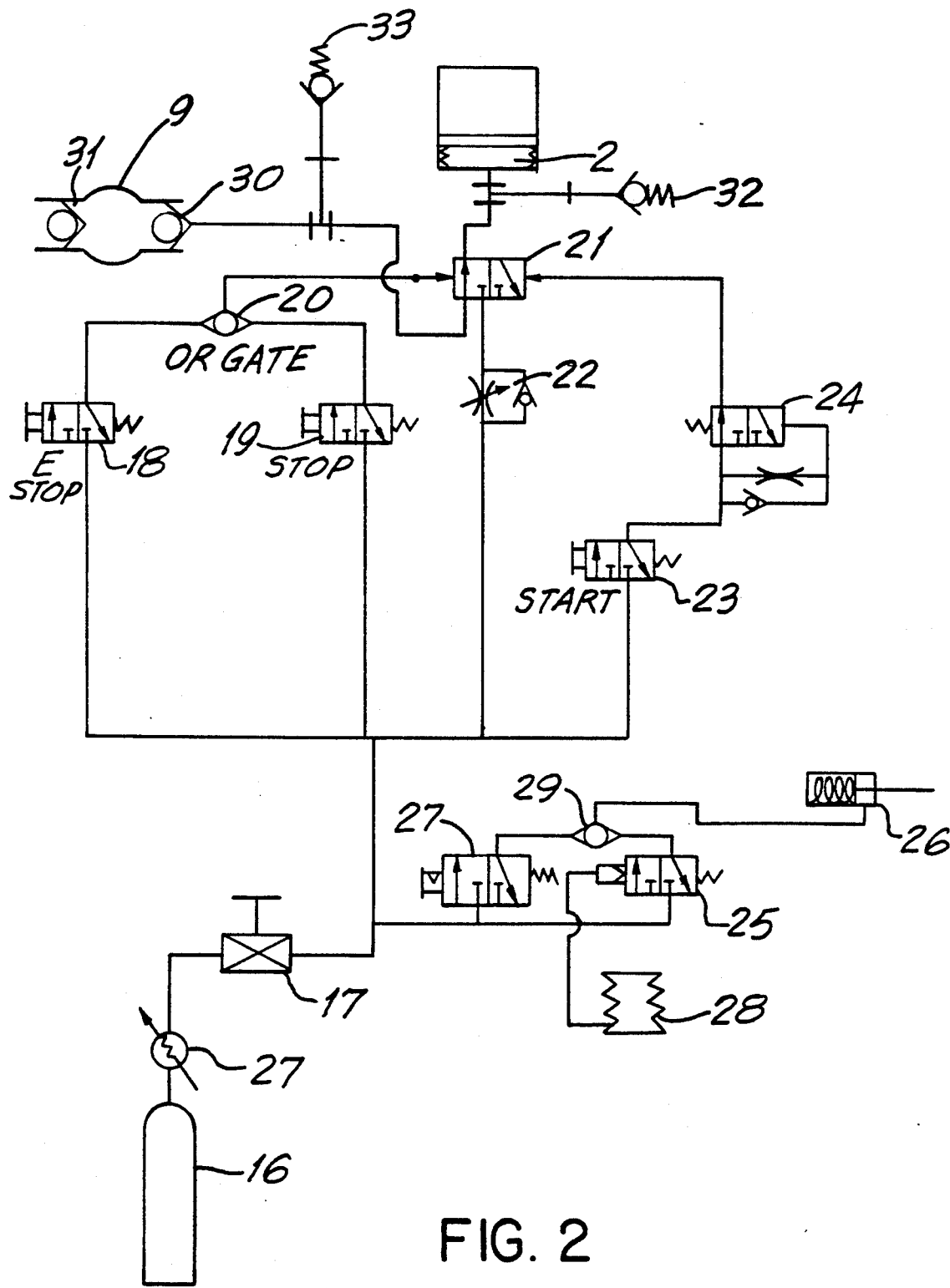
FIG. 2 is a schematic of the pneumatic system of the present invention.

Cylinder 16, as hereinafter explained, is connected to carbon dioxide reservoir 2 as shown in FIG. 2. The pressure of the carbon dioxide in cylinder 16 must be lowered before the carbon dioxide is introduced into the patient and, further the pressure must be reduced before the carbon dioxide is introduced into reservoir 2. To accomplish this the carbon dioxide from cylinder 16, at the initiation of a procedure, flows through a pressure regulator 27 which reduces the pressure of the carbon dioxide to about 50 psi. While a patient can be harmed by pressures, in excess of 2 psi, the components of system 1 would be harmed by pressures in excess of 170 psi. Reservoir 2 includes a thin walled bellows 2a which rides within a cylindrical housing 2b. In the preferred embodiment bellow 2a is formed of polyurethane but it may be formed of other appropriate flexible polymeric materials with low permeability to carbon dioxide such as mylar. Disc 3 rides on top of bellows 2a, exerting a constant pressure thereon. As a consequence of this, pressure in the reservoir remains constant throughout the full range of motion of the bellows. Thin walled bellows 2a has a wall thickness, in the preferred embodiment, of about 0.005 inches but the thickness of the wall may range between about 0.001 inches to 0.010 inches. If the wall is too thin it is too fragile and if it is too thick it will not fully collapse when emptied during a procedure.

Filling of reservoir 2 is initiated by actuating a three port, two way, spring return, start valve 23. In response to actuating start valve 23, a positive pressure burst of carbon dioxide is delivered to a pneumatic one-shot valve 24 which issues a short positive pressure burst of carbon dioxide from its outlet when it receives a positive pressure burst of carbon dioxide at its input. As a safety mechanism, valve 24 issues only a single burst of gas in response to each burst of gas issued from valve 23 and thus if a user inadvertently leaves start valve 23 activated excess gas is not delivered to the reservoir.

The output from valve 24 is used to pilot a double air piloted, three port, two-way valve 21 into a position which initiates the filling of reservoir 2. Once valve 21 is in its filling position, carbon dioxide from cylinder 16 passes into the reservoir 2 after first passing through a flow restrictor 22 and valve 21. Flow restrictor 22 serves as a means for controlling the fill rate of reservoir 2.

An actuating arm 4 is associated with reservoir 2. Filling of reservoir 2 stops when disc 3 contacts actuating arm 4. In use, as bellows 2a fills with carbon dioxide, disc 3 rises until it contacts actuating arm 4. Actuating arm 4 passes through a protective sleeve 5. Actuating arm 4 is coupled, via a lever linkage, to a mechanically actuated, spring return, three port two-way stop valve 19. When actuated, valve 19 issues a positive pressure gas pilot signal to valve 21 shutting off the reservoir filling process. The filling of reservoir 2 can also be halted by mechanically actuated, spring return, three port, two-way valve 18. Valve 18 also causes a positive pressure pilot signal to be sent to valve 21. Output from either valve 18 or valve 19 is directed to valve 21 through air logic exclusive OR gate 20 to insure the output gas from valves 18 and 19 are directed to valve 21 rather than being vented to atmosphere. In the preferred embodiment of the invention, the carbon dioxide in reservoir 2 is held at a pressure of about 0.019 psi (1 mmHg). However, the carbon dioxide in reservoir 2 may have a maximum pressure of 0.77 psi and a minimum pressure of 0.

During a barium enema study, carbon dioxide is drawn out of reservoir 2 and insufflated into a patient using a conventional hand actuated insufflation bulb 9. Hand actuated insufflation bulb 9 provides the doctor with a highly controllable mechanism for slow insufflation of the carbon dioxide. It also provides tactile feedback so that the physician is aware of increasing pressures or obstructions.

Bulb 9 is an egg-shaped element, preferably made of plastisol. Bulb 9 has a one-way check valve mounted in both of its ends. The check valves are oriented such that squeezing of bulb 9 directs flow out of a spring biased valve 31, while releasing of bulb 9 draws gas into the bulb from valve 30. Valve 31 insures that gas in the reservoir does not freely leak therefrom. Bulb 9 is connected to both enema tip 10 and system 1 via PVC tubes 8a, 8b.

Barium sulfate solution, for delivery to a patient, is held in a conventional bag 14. Bag 14 is connected to enema tip 10 via tubing 12. The control of the flow of the barium is effectuated using a pneumatically actuated pinch valve 13 which is comprised of a single rod end spring biased air cylinder 26. Pinch valve 13 is used to shut the flow of barium sulfate through tubing 12. Pinch valve 13 is a normally closed valve. Pinch valve 13 can be opened in two ways. Pinch valve 13 opens in response to pressure exerted on foot pedal 28 which is a closed end pneumatic bellows as shown in FIG. 2. Pedal 28 is coupled to valve 25, a three port, two-way actuator with spring return. A mechanically actuated three port, two-way valve with mechanical detent is also provided as a means to open valve 13. Valve 27 can be used if the physician does not want to use foot pedal 28. Output from valve 25 and 27 pass through an air logic exclusive OR gate 29 before going to air cylinder 26. This ensures that the output from valve 25 has not vented to the atmosphere through valve 27 or vice versa. System 1 integrates the delivery mechanisms for both the carbon dioxide and the barium suspension. This frees the clinician's hands allowing more attention to be directed to the patient.

System 1 is provided with a variety of safety mechanisms. Some of these safety mechanisms are provided by redundencies which insure patient isolation from the high pressure gas even under any single fault condition. Carbon dioxide flow into either reservoir 2 or the patient must pass through valve 21. Thus, if valve 21 is in its reservoir filling position, carbon dioxide cannot be directed to the patient and if valve 21 is in position to deliver carbon dioxide to the patient, reservoir 2 is isolated from cylinder 16. Thus the high pressure carbon dioxide cannot be mistakenly directly to the patient. As an additional safety mechanism the pressure of the carbon dioxide in reservoir 2 is limited to the pressure generated by the weight of disc 3 distributed over the cross sectional area of the reservoir. The components of this system are sized such that the pressure in reservoir 2 is far below the pressure that would injure the colon. In the preferred embodiment of the invention disc 3 has a weight of about one pound; housing 2b has a diameter of about 6 inches and bellows 2a has a diameter of between 4 inches to 6 inches. In one embodiment the diameter of the bellows is 5.75 inches. Redundancies are provided to insure that reservoir 2 cannot overfill. In the event that valve 19 were to fail to stop the reservoir from filling and the user did not halt the gas flow with valve 18, excess carbon dioxide would be vented to atmosphere through check valve 32. Additionally, if a leak develops across the spool of valve 22, excess gas will be vented to atmosphere through check valve 33. These features maintain isolation of the patient from the high pressure carbon dioxide. Further, in response to actuation of the start valve, reservoir 2 fills with a fixed volume of carbon dioxide gas. This limits the volume of gas that can be delivered to the patient absent a conscious decision made by the clinician to deliver more.

In the preferred embodiment of the invention, a ¼ turn ball valve 17 is provided for shutting off high pressure gas to the system's components. Controls 7 for controlling the filling of reservoir 2, loading of the pinch valve, and shutting off the high pressure container are all conveniently mounted on the side of the housing 6. System 1 is mounted on casters 30 to aid in positioning the system in the radiology suite. System 1 is provided with an integral IV pole 15 to help in suspending the barium sulfate suspension.

All of the energy needed to run system 1 is derived from the compressed carbon dioxide. This obviates the need for electrical connections which simplifies the use of the system, keeps the cost of the system relatively low, and does away with safety concerns associated with electrical systems.

What is claimed:

1. A gas delivery system for use with an enema insufflation system including a source of barium sulfate solution and a source of gas both connected, via tubing, to an enema tip, the enema tip constructed to allow alternate delivery of the barium sulfate solution and the gas to a patient to enable performance of a double contrast barium enema study, the gas delivery system comprising:

a carbon dioxide reservoir including a non-elastic collapsible container means for holding a predetermined volume of carbon dioxide at a relatively low constant pressure;

means for connecting said reservoir to said source of gas, said gas being compressed carbon dioxide;

an insufflation means coupled to said carbon dioxide reservoir to draw carbon dioxide from said reservoir for a delivery, through the enema tip, to the patient; and means to functionally isolate said source of compressed carbon dioxide from the patient.

2. The system of claim 1 wherein said means to functionally coalate comprises a single valve having a fill position and an empty position, said valve controlling the filling and emptyinq of said reservoir, said valve when in said fill position not permittinq said reservoir to empty, said valve when in said empty position not permitting said reservoir to fill.

3. The system of claim 1 wherein said source of compressed carbon dioxide contains liquified carbon dioxide.

4. The system of claim 1 wherein said source of compressed carbon dioxide contains carbon dioxide at a pressure of about 840 psi.

5. The system of claim 1 wherein said carbon dioxide, in said reservoir, is held at a pressure of less than 0.77 psi.

6. The system of claim 5 wherein said carbon dioxide in said reservoir is held at a pressure of about 0.019 psi.

7. The improved system of claim 1 and further including a pressure regulator positioned down stream of said carbon dioxide source to reduce the pressure of said carbon dioxide.

8. The system of claim 7 and further including a flow restrictor functionally connected to said pressure regulator, said flow restrictor controlling the flow rate of carbon dioxide into said carbon dioxide reservoir.

9. The system of claim 1, wherein said non-elastic collapsible container includes a thin walled bellows and a weighted cover, said weighted cover moving in response to the filling and emptying of said thin walled bellows with said gas.

10. The system of claim 9 wherein said bellows is formed of a flexible polymeric material having a low permeability to carbon dioxide.

11. The system of claim 10 wherein said polymeric material is polyurethane.

12. The system of claim 9 wherein said bellows has a wall thickness of between about 0.001 inches and 0.010 inches.

13. The system of claim 12 wherein said bellows has a wall thickness of about 0.005 inches.

14. The system of claim 9 and further including a first stop means to stop the filling of said carbon dioxide reservoir.

15. The system of claim 14 and further including additional stop means to stop the filling of said carbon dioxide reservoir.

16. The improved system of claim 8 wherein the pressure of carbon dioxide in said thin walled bellows is limited to the pressure generated by the weight of said weighted cover distributed over the cross sectional area of the thin walled bellows.

17. The improved insufflation system of claim 16 wherein said thin walled bellows has a diameter of between about 4 inches and about 6 inches and said weighted cover has a weight of about 1 pound.

18. The insufflation system of claim 17 wherein said bellows has a diameter of about 5.75 inches.

19. The system of claim 9 further including a housing for said source of gas, said housing having an interior and an exterior and the controls for controlling the system are mounted on the exterior of the housing.

20. The system of claim 19 wherein said housing is mounted on casters to aid in positioning of the system in a radiology suite.

21. The system of claim 1 and further including a first stop means to stop the filling of said carbon dioxide reservoir.

22. The system of claim 21 wherein said first stop means includes a stop valve and an actuating arm connected to said stop valve.

23. The system of claim 1 and further including starting means for initiating filling of said carbon dioxide reservoir with said carbon dioxide.

24. The system of claim 23 wherein said starting means includes three valves, a first valve for issuing a positive pressure burst, a second one-shot valve which issues a single short positive pressure burst from its outlet when it receives the positive pressure burst at its input and a third valve which in response to an output from said second valve initiates filling of said carbon dioxide reservoir, said second one-shot valve issuing only said single burst of gas in response to each burst of gas issued from said first valve to avoid excess gas being delivered to the system if a user inadvertently leaves said first valve actuated.

25. The system of claim 1 wherein said insufflation means is a hand activated bulb.

* * * * *